(12) United States Patent
Ho et al.

(10) Patent No.: US 8,784,436 B2
(45) Date of Patent: Jul. 22, 2014

(54) MEDICAL INSTRUMENT FOR SETTING TISSUE CLIPS

(75) Inventors: Chi-Nghia Ho, Stuttgart (DE); Gunnar Anhoeck, Reutlingen (DE); Franziska Baur, Dettingen unter Teck (DE); Marc O. Schurr, Tuebingen (DE); Ruediger Prosst, Stuttgart (DE); Thomas Gottwald, Kochel am See (DE)

(73) Assignee: Ovesco Endoscopy AG, Tuebingen (DE)

( * ) Notice: Subject to any disclaimer, the term of this patent is extended or adjusted under 35 U.S.C. 154(b) by 634 days.

(21) Appl. No.: 12/914,938

(22) Filed: Oct. 28, 2010

(65) Prior Publication Data

US 2011/0152888 A1    Jun. 23, 2011

(30) Foreign Application Priority Data

Oct. 30, 2009    (DE) .................. 10 2009 051 408

(51) Int. Cl.
*A61B 17/10*    (2006.01)
(52) U.S. Cl.
USPC ........................................... 606/142
(58) Field of Classification Search
None
See application file for complete search history.

(56) References Cited

U.S. PATENT DOCUMENTS

| 5,556,416 A * | 9/1996 | Clark et al. ............ 606/205 |
| 7,850,600 B1 * | 12/2010 | Piskun .................. 600/114 |
| 2002/0062130 A1 | 5/2002 | Jugenheimer | |
| 2003/0028207 A1 | 2/2003 | Lang | |
| 2005/0177168 A1 | 8/2005 | Brunnett | |
| 2005/0283189 A1 | 12/2005 | Rosenblatt | |
| 2008/0249561 A1 | 10/2008 | Stokes | |
| 2010/0234687 A1 | 9/2010 | Azarbarzin et al. | |

FOREIGN PATENT DOCUMENTS

| DE | 196 18 291 A1 | 1/1998 |
| DE | 198 34 263 A1 | 2/2000 |
| DE | 100 55 923 A1 | 2/2003 |
| DE | 20 2008 007 774 U1 | 9/2008 |
| EP | 0 634 146 A2 | 1/1995 |
| WO | WO 9925255 A1 | 5/1999 |
| WO | 03/026516 A1 | 4/2003 |
| WO | 2007/025296 A2 | 1/2007 |
| WO | WO 2009/073577 | 6/2009 |
| WO | WO 2009/150186 A1 | 12/2009 |

OTHER PUBLICATIONS

German Patent Office, German Examination Report for DE10 2009 051 408.2-35, Aug. 25, 2010, Germany.

(Continued)

*Primary Examiner* — Corrine M McDermott
*Assistant Examiner* — Son Dang
(74) *Attorney, Agent, or Firm* — AlbertDhand LLP

(57) ABSTRACT

A proctological instrument is disclosed comprising an instrument handle to which at its proximal end a bending-resistant tubular shaft is mounted at the distal end of which a cap is fixed or formed to which a tissue clip adapted to be withdrawn from the cap by means of a releasing or withdrawing device is attached in a preferably spring-elastic manner. In accordance with the invention, the tubular shaft is offset at its distal end portion in an area directly ahead of the cap and/or the cap itself is offset at a predetermined fixed angle so that the withdrawing direction for the clip defined by the cap is aligned at the angle with respect to the tubular shaft axis.

9 Claims, 8 Drawing Sheets

(56) References Cited

OTHER PUBLICATIONS

Figure 1:
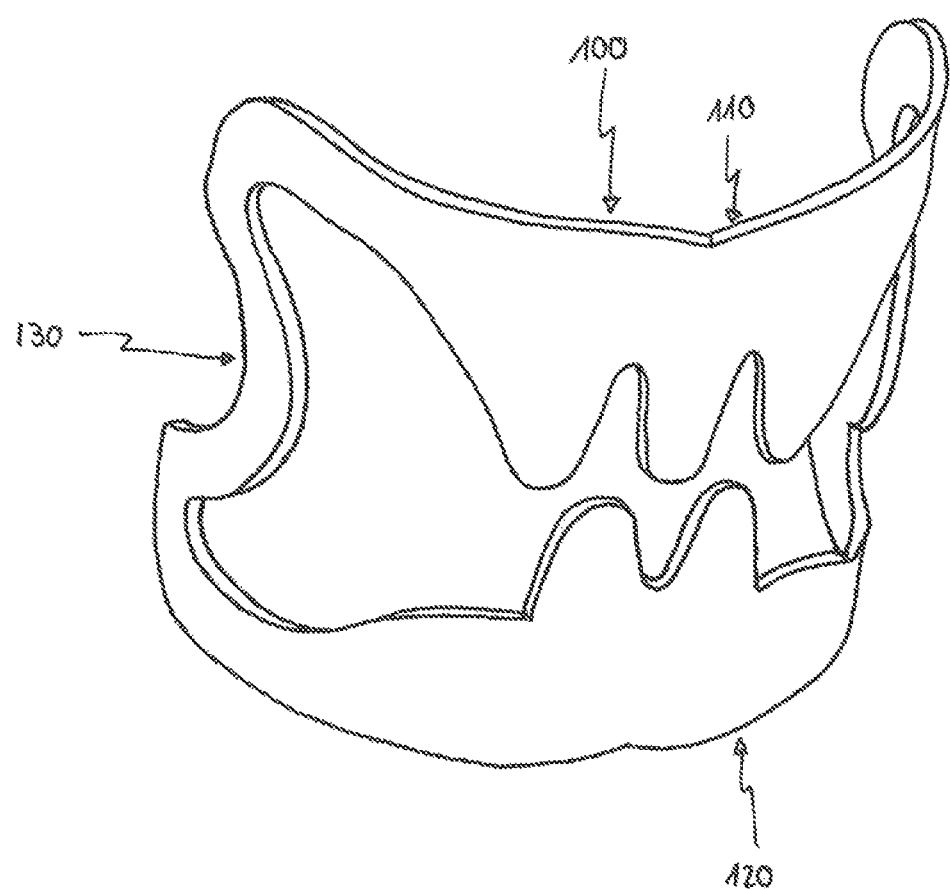

European Search Report for EP Application 10188207.4, Feb. 15, 2011.

German Patent Office, Examination Report for DE 10 2009 051 408.2, Oct. 9, 2013.

Japanese Examination Report for Application No. JP 2010-242901, Apr. 11, 2014.

* cited by examiner

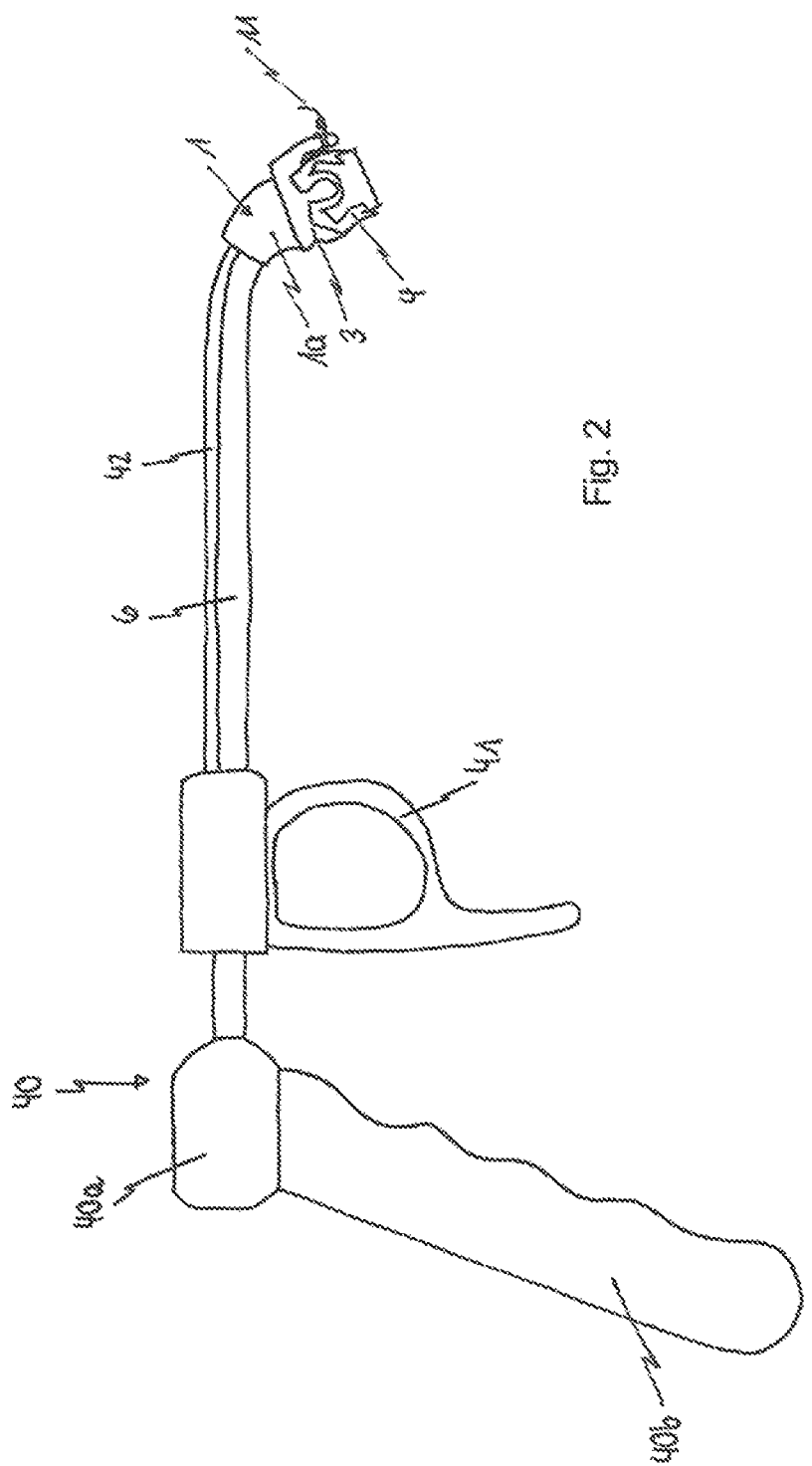

MEDICAL INSTRUMENT FOR SETTING TISSUE CLIPS

The present invention relates to a medical, preferably proctological instrument for setting tissue clips.

Such instrument makes use of a shaft-type feed means for a tissue clip for closing tissue damage such as, for instance, an anal fistula and similar pathologic tissue changes.

From the state of the art, for instance according to U.S. Pat. No. 6,849,078 B2, a tissue clip of this species is generally known as regards its basic construction. For a better comprehension, this clip is hereinafter described in more detail with reference to FIG. 1.

Accordingly, such clip 100 consists of a mouth-like clamping means having two toothed jaws 110, 120 which can be opened and shut via two lateral hinges 130 or via flexible moldings. The hinges 130 or the flexible moldings are preferably formed of spring-elastic straps which when opening the jaws 110, 120 store spring energy which results in snapping to close the jaws 110, 120 with a predetermined clamping force when the jaws 110, 120 are released, i.e. when the hinges 130 or the flexible moldings are actuated.

In detail, each clip 100 is punched or lasered in one piece out of a spring steel sheet by working a ring having a partially different ring width out of the spring steel sheet. Two diametrally opposed ring portions having a large ring width constitute the two jaws 110, 120, whereas the two ring portions disposed there between having a narrow ring width form the hinges 130 or the flexible (elastic) moldings. The jaws 110, 120 are formed by arching the ring portions having a large ring width in a curved shape over the flat side thereof, whereas the two ring portions having a narrow ring width are twisted about their longitudinal axis by approx. 180° in order to form the hinges. This special shaping of the lasered spring steel sheet creates the shape of a type of shark mouth having two rows of teeth moving toward each other which are formed by laser welding the ring portions having a large ring width.

The functioning of the afore-described medical tissue clip 100 can be described as follows:

In general, an endoscopic implantation of a medical device in total constitutes the most tolerable process for a patient. In this case, the medical device must be fixed from the inside of a hollow organ to the latter. For this purpose, a number (at least one) of the afore-described tissue cleats, clips or anchors are inserted into the hollow organ by means of an endoscope or a similar shaft-type feed means and are positioned at predetermined sites at the inner side of the organ. To this end, the respective clip or anchor is brought close to the organ tissue and the biasing spring is released for a snapping of the clip or clamping of the anchor. The latter then holds or clamps a tissue fold between its jaws or its hook or needles with a predetermined clamping or expanding force, wherein the teeth, hooks, needles or jags of each jaw cut into the tissue and preferably penetrate the same.

The endoscope or shaft-type feed means not shown in detail in FIG. 1 usually is equipped with an endoscope head or an endoscope cap which includes, apart from the functions generally required for an endoscope such as lighting, optical system and rinsing means, if necessary, in addition a holding and withdrawing means for the tissue clip. It is referred in this context to the fact that in this entire application also a simple inserting aid without separate lighting and optical system as well as rinsing function can be understood by an endoscope.

The holding and withdrawing means substantially consists of an expanding sleeve as well as a slide operable manually or by remote control which is movable in the longitudinal direction of the endoscope. The expanding sleeve is designed such that the already opened tissue clip can be placed onto the sleeve so that the clip can be prevented from slipping backward while being inserted into the hollow organ. For this purpose, the slide is positioned axially behind the clip and serves so-to-speak as an axial stop for the clip.

As soon as the clip is to be positioned at a particular site, the slide is moved axially forward and in so doing strips off the clip over the expanding sleeve. The clip is actuated, i.e. the biasing mechanism within the clip described before by way of FIG. 1 is released when it is stripped off the expanding sleeve and the two jaws of the tissue clip snap to close while clamping the tissue provided there between. It has turned out, however, that the exact setting of the tissue clip by the known device is very difficult especially in the vicinity of the sphincter muscle.

In view of this state of the art, it is therefore the object of the present invention to provide a medical, preferably proctological instrument for setting tissue clips by means of which a tissue clip or a tissue cleat can be easily and safely set in the vicinity of the sphincter muscle in the inner organ wall (colon wall).

This object is achieved by a medical, preferably proctological instrument comprising the technical features according to claim 1. Advantageous configurations of the invention constitute the subject matter of the subclaims.

In accordance with the invention, the proctological instrument includes an instrument handle to which a rigid tubular shaft is mounted at its proximal end at the distal end of which a cap is fixed or formed to which a tissue clip adapted to be withdrawn from the cap by means of a releasing and withdrawing device is attached in a preferably spring-elastic manner. Either the cap itself or the tubular shaft is offset at its distal end portion in an area directly ahead of the cap at a predetermined fixed angle (>0°) so that the withdrawing direction for the clip defined by the cap is aligned at such angle with respect to the tubular shaft axis. In this way, the cap can be attached better to the surface of the organ wall and thus the clip can be positioned more exactly. The expression "rigid" is defined as the capability not get deformed in practical use like metal, aluminium hard resign, etc. In other words, the rigidity of the shaft is much higher than that of body tissue of a patient.

The releasing or withdrawing device is preferably formed to include a pull or push element extending along the tubular shaft in at least one outer function channel fixed at the tubular shaft and being coupled to an operating lever at the instrument handle. Advantageously the pull or push element is connected at its distal end to a strip ring which is seated to be longitudinally movable on the cap and by means of which the clip can be withdrawn. In this way the clip can be prevented from twisting during the withdrawing operation.

It is further advantageous to design the tubular shaft at its distal end portion immediately ahead of the cap in S-shape, wherein the withdrawing direction of the cap extends at the fixed angle with respect to the imaginary straight central axis of the tubular shaft. The S-shape resets the cap in parallel to the imaginary central axis (i.e. it projects less to the side) and thus can be better inserted into the hollow organ.

Figure 2A:
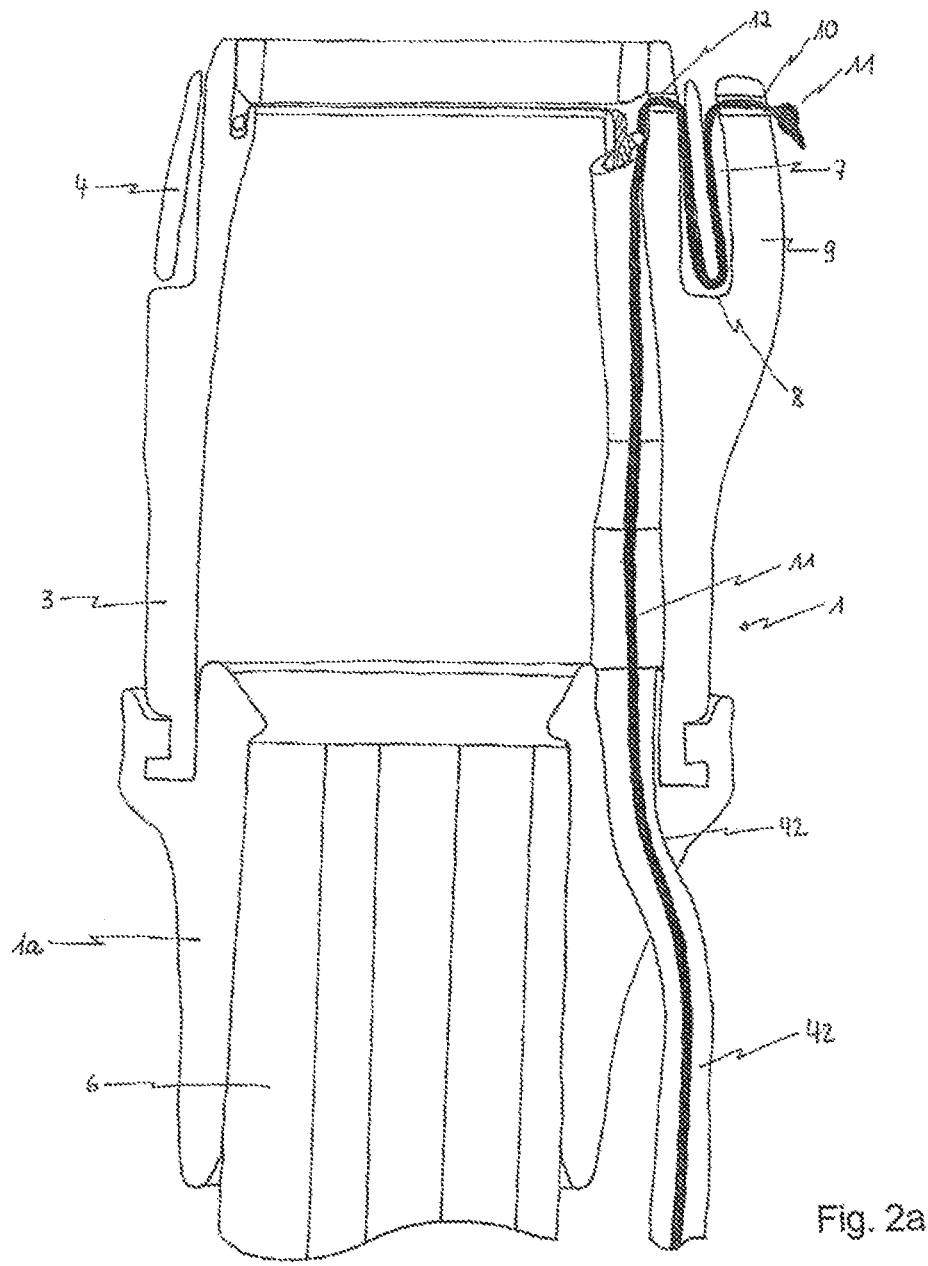
Figure 3:
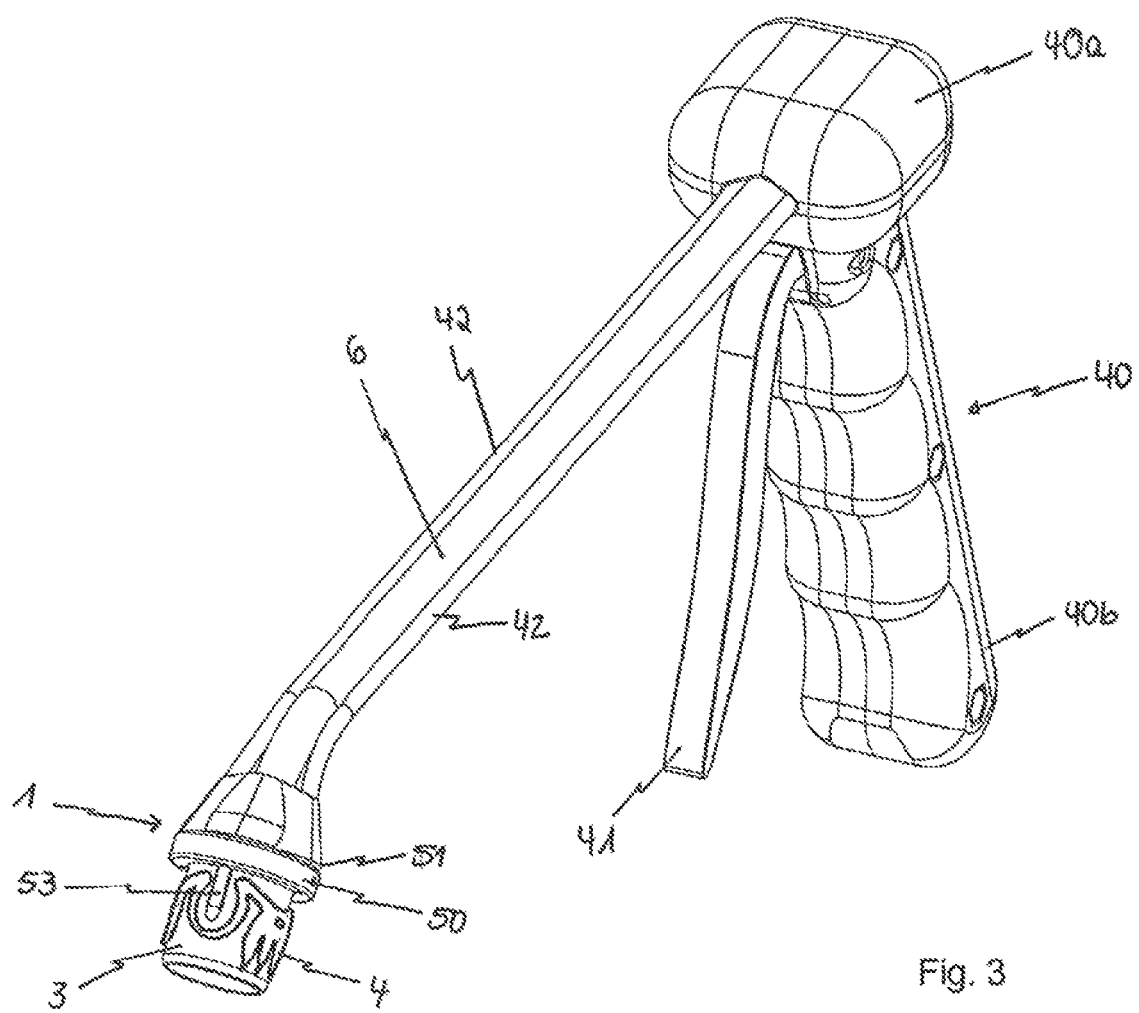
Figure 4:
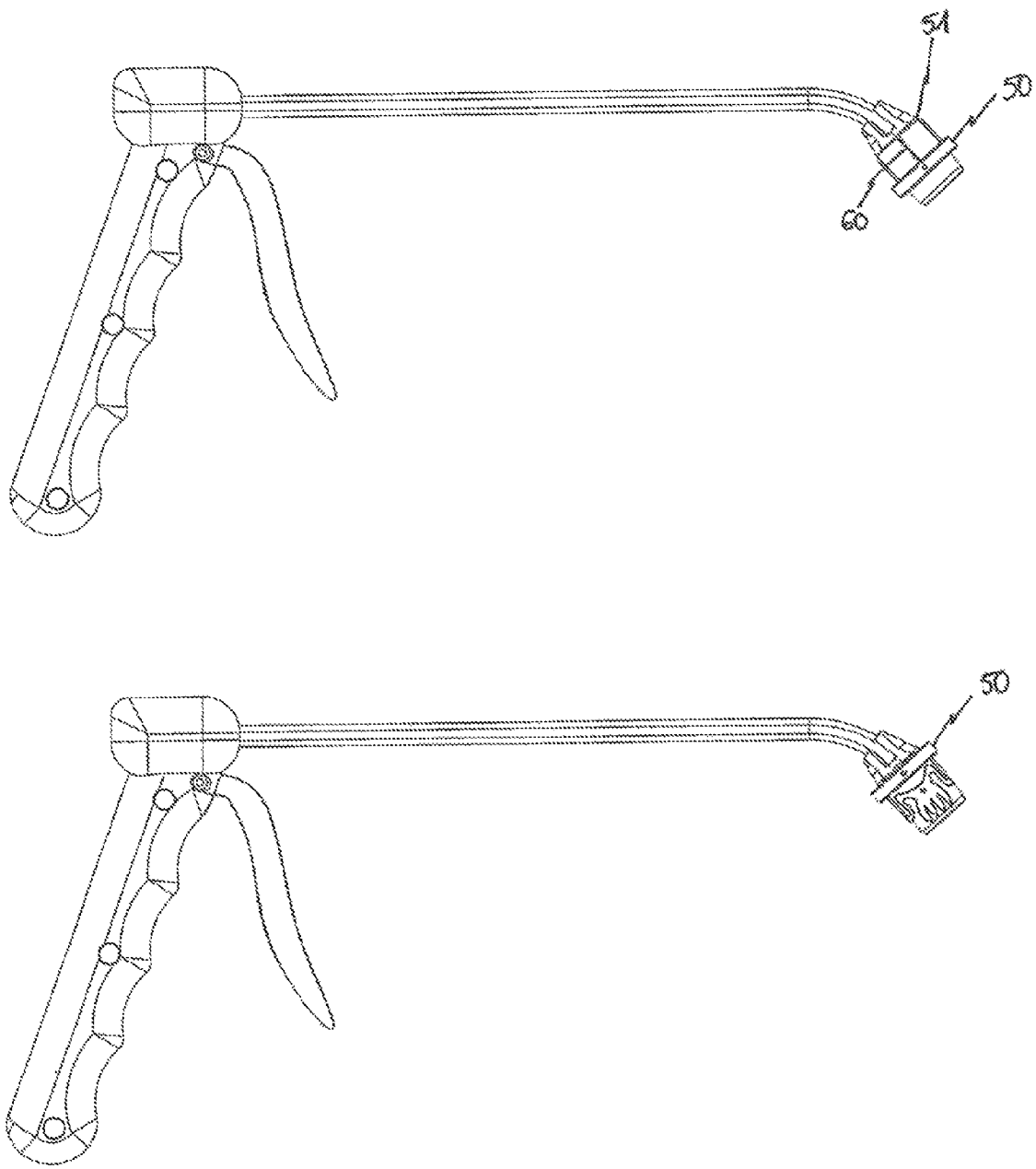
Figure 5:
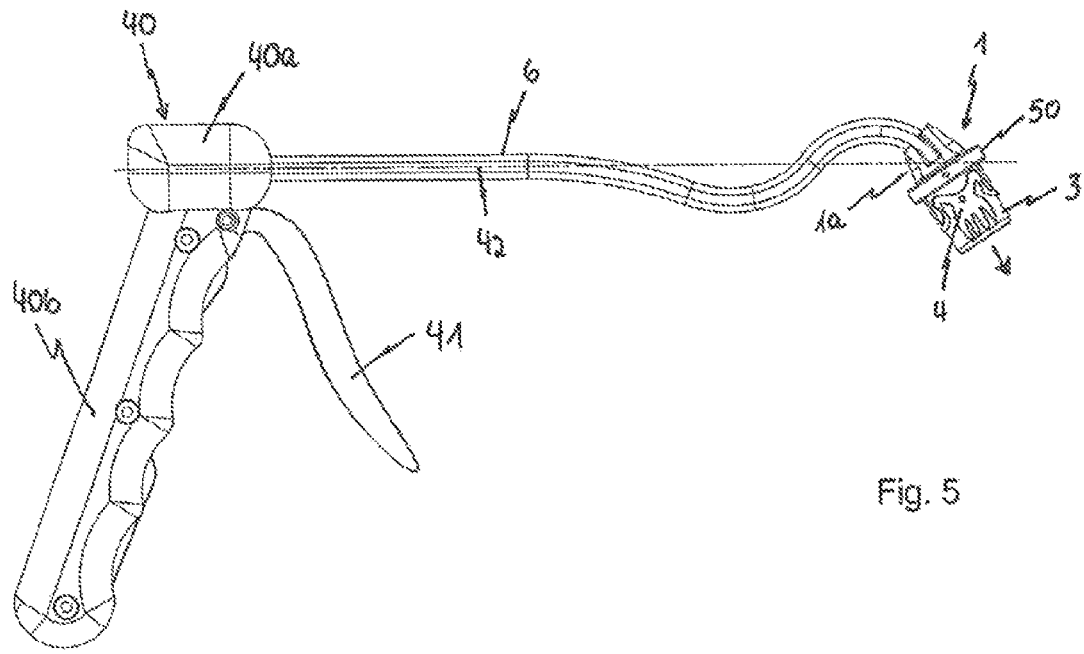
Figure 6:
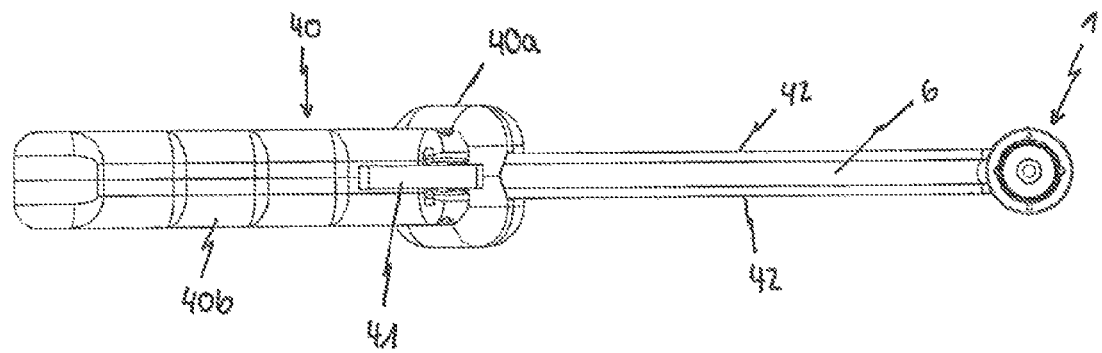
Figure 7:
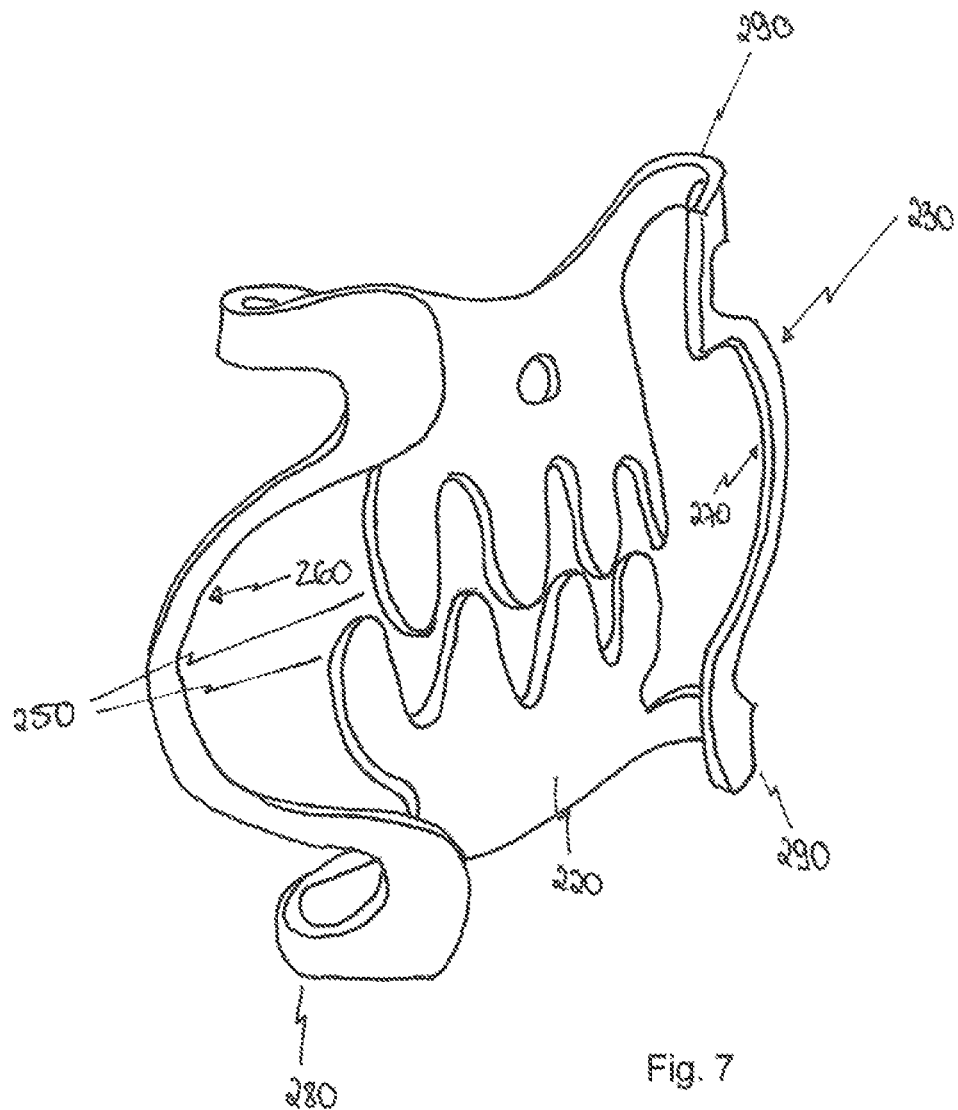
Figure 8:
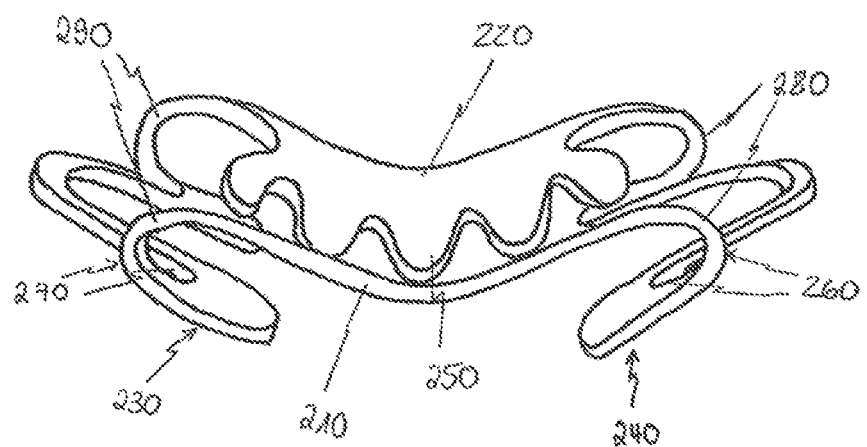

Hereinafter the invention shall be explained in detail by way of preferred embodiments with reference to the accompanying figures, in which FIG. 1 illustrates the exemplary construction of a tissue clip as it is known already from the state of the art and as it can equally be used in the present invention, FIG. 2 is a side view of a medical instrument according to a first preferred embodiment of the invention, FIG. 2a illustrates the magnified distal end portion of the medical instrument according to FIG. 2, FIG. 3 is a perspective view of a medical instrument according to a second preferred embodiment of the invention, FIG. 4 is a side view of the medical instrument according to FIG. 3 including the attached tissue clip and the discharged tissue clip, FIG. 5 is a side view of a medical instrument according to a third preferred embodiment of the invention, FIG. 6 is a bottom view of a medical instrument according to a fourth preferred embodiment of the invention, FIG. 7 is a perspective view of a tissue clip according to a preferred embodiment of the invention which is developed especially for treating anal fistulae and FIG. 8 is a top view of an alternative configuration of the tissue clip according to FIG. 7.

In accordance with FIGS. 2 and 2a, the medical (proctological) instrument comprises a preferably rigid or bending-resistant tubular shaft 6 (for instance made of corrosion-resistant steel) at the proximal end of which an operating handle 40 is mounted and at the distal end of which a shaft head 1 including a releasing or withdrawing device for a tissue clip 4 attached thereto is mounted.

The handle 40, preferably manufactured of a plastic cast part, includes a mounting portion 40a into which the tubular shaft 6 is inserted, pressed, clamped or cast and a holding portion 40b extending at an angle with respect to the tubular shaft 6. Moreover an operating lever 41 is provided which is either guided along the tubular shaft 6 to be movable on the same or is hinged to the holding portion 40b of the handle 40. The movably guided operating lever 41 is coupled directly and the hinged operating lever 41 is coupled via a gear train or similar movement transfer or deflection mechanism (not shown) to a pull and/or push element 11 which in the present case is supported along the tubular shaft 6 in a guide 42 fixed to the tubular shaft 6, for instance in the form of a Bowden cable. The pull and/or push element 11 in turn is coupled to a tissue clip discharge means by which a tissue clip 4 slipped onto the shaft head 1 preferably in a spring-elastic manner is slipped on in the design afore-described by way of FIG. 1.

Concretely speaking, the shaft head 1 according to FIG. 2a consists of a type of cap (made of plastic material) having a slip-on portion 1a (preferably a silicone nozzle) which in the mounted state encompasses the distal end portion of the rigid tubular shaft 6.

The cap 1 is formed at an axial distance from the slip-on portion 1a at the sheath side into or including an expanding sleeve (expanding sleeve portion) 3 which, in the present embodiment, is positively connected (clipped) to the slip-on portion 1a. It can also be integrally connected to the slip-on portion 1a or glued or welded to the same. The tissue clip 4, as described in detail in the foregoing by way of FIG. 1 and thus likewise belonging to the subject matter of the invention, is adapted to be pushed onto the expanding sleeve 3. The expanding sleeve 3 axially projects from the distal end face of the tubular shaft 6 and thus forms a cup-shaped sleeve portion radially outwardly rounded at its front edge.

Preferably the slip-on portion la is frictionally slipped onto the distal end piece of the tubular shaft 6. But it may also be glued, pressed or cast with the tubular shaft 6.

The expanding sleeve 3 according to the invention includes a front groove 7 introduced in axial direction from its distal end face in the sheath-side cap or sleeve wall, which front groove preferably opens as a pitch circle or sickle-shaped (circumferential) slit at the distal front side of the expanding sleeve 3 and the groove bottom thereof forms a stop 8 at an axially rear position, preferably approximately at an axially central portion of the expanding sleeve 3. The radius of the front groove 7 is selected to be larger than the outer radius of the expanding sleeve 3, however, so that when forming the front groove 7 two slits appropriately spaced in circumferential direction are imparted to the sleeve wall. By forming these front groove slits the cap sheath wall is thus longitudinally split in this area, whereby a type of tab or tongue 9 defining the radially outer groove wall is formed at the outside of the cap wall.

Another variant of providing a front groove according to the above definition is the additional arrangement of a tab or tongue preferably curved in axial direction, as this is shown especially in FIG. 2a, whose root is formed integrally with the cap and which extends axially in the direction of the expanding sleeve at a radial distance from the cap sheath wall while forming the groove. Consequently, in this case the sheath wall is not split (as described before), but an additional component in the form of the tab is guided over the sheath wall of the cap. This tab can have so narrow dimensions that it remains straight (without radius) in cross-section, i.e. it need not necessarily follow the circumference of the cap. Moreover, the ground plan shape of the tab can be designed largely at will, i.e. it can be thickened and/or widened in the direction of the tab root (transition area between the tab and the cap) in order to obtain higher stiffness. Also the tab root itself can be freely dimensioned and designed according to static aspects so as to reach maximum stiffness.

Irrespective of the fact according to which manufacturing variant the tab 9 is finally formed, according to the invention it extends from the groove bottom constituting the stop 8 in the direction of the distal end face of the cap 1 or the expanding sleeve 3, wherein the rounded free front edge thereof is axially slightly reset vis-à-vis the distal front edge of the expanding sleeve 3.

As at least indicated in FIG. 2a, the front groove 7 does not extend exactly in parallel to the central axis of the cap but is inclined in the direction of the distal end face toward the central axis so that an inserted clip 4 can slip off more easily to the front. Moreover, the groove 7 is not straight but the groove walls thereof, at least the outer groove wall, are slightly curved in axial direction such that the groove 7, at least the tab 9, arches radially outwardly at its axial central portion. In this way, the design according to FIG. 1 geometrically allows or facilitates in this state already the folding behavior of a slipping tissue clip 4.

At an axial front end portion of the tab 9, the same is provided with a radial outer through bore 10 through which a thread 11, cable or tissue is guided from the inside of the groove toward the outside of the cap 1 and is fixed there. The thread 11, cable or tissue constitutes the afore-mentioned pull element. Preferably, for this purpose the one thread end is knotted to the outside of the tab so that the thread 11 is prevented from withdrawing through the radial through bore 10. Moreover, at a position substantially radially opposed to the afore-mentioned through bore 10, i.e. in the distal end area of the axially projecting expanding sleeve 3, the cap 115 provided with a radial inner through bore 12 through which the thread 11 is guided from inside the groove into the interior of the expanding sleeve 3. In this case the thread portion crossing the groove forms the said releasing or withdrawing device for the clip.

As one can infer especially from FIG. 2a, the inner through bore 12 is provided axially ahead of the distal end side of the tubular shaft 6 so that the thread 11 emerging from the inner through bore 12 can be threaded into a function channel (guide) 42 opening at the shaft end face and extending at the outside of the tubular shaft 6, the function channel constituting the afore-mentioned guide of the pull element 11.

The tubular shaft 6 is moreover offset or bent in the area of its distal end portion (i.e. in an area directly ahead of the cap 1) so that the discharge direction for the tissue clip 4 defined by the expanding sleeve 3 extends at a (fixed) angle (>0°) with respect to the tubular axis.

The operating mode of the medical instrument according to the invention including the holding and withdrawing function for the tissue clip 4 is described hereinafter in detail.

In order to move a tissue clip 4, for instance according to FIG. 1, to its predetermined position, first of all it has to be pulled onto the expanding sleeve 3 of the shaft cap 1. For this purpose, the lower and upper jaws of the tissue clip 4 are manually opened so that the clip 4 can be attached to the rounded front edge of the expanding sleeve 3 and can be pushed over the same. The rear edge of the tissue clip 4 penetrates the front groove 7 of the shaft cap 1 and pulls the thread 11 out of the function channel 42 provided at the instrument shaft 6.

Finally, the pushing movement of the clip 4 comes to a standstill when it contacts the groove bottom 8, wherein the clip 4 and the entrained thread 11 adopt the position shown in FIG. 2. That is to say, at this position the clip 4 is completely pulled onto the cap 1 and in this way can be introduced via the tubular shaft 6 into a hollow organ.

The thread 11 encompasses the rear edge of the clip 4 and thus is given a U-shape viewed in the longitudinal direction of the thread.

As soon as the proctological instrument according to the invention has reached a diseased site within a hollow organ, the expanding sleeve 3 is pressed against the organ wall. If the clip 4 is to be stripped off, the thread 11 which is guided through the function channel 42 to the proximal operating lever 41 is pulled by longitudinal displacement of the operating lever 41, wherein the thread portion crossing the front groove 7 in radial direction shrinks. Since the thread 11 is fixed in the outer through bore 10, it exerts a force in axial direction on the clip 4 at an appropriate ratio according to the block and tackle principle, whereby the clip 4 is displaced in the direction of the distal end of the endoscope cap 1. The outer rounding of the front expanding sleeve edge and the smooth, viz. arched molding of the front groove 7 (especially the tab 9) facilitate sliding of the clip 4 over the front edge of the expanding sleeve 3 and further reduce the maximum displacing force to be applied via the thread 11. As soon as the rear edge of the clip 4 has left the front groove 7 and therefore can no longer be held by the tab 9, the biasing force stored in the clip 4 causes the clip 4 to come off the expanding sleeve 3, thereby the organ wall being pinched off in the area directly ahead of the expanding sleeve 3.

In this context, it is further referred to the fact that, instead of the movably supported operating lever 41 according to FIG. 2, there may also be provided a lever 41 hinged at the holding portion of the handle 2 according to FIG. 3 at which the thread 11 is articulated such that it is pulled toward the holding portion 40*b* when the lever 41 is swiveled.

FIGS. 3 and 4 show another embodiment of the invention, wherein hereinafter merely the features that are different from the above embodiments shall be discussed.

As one can infer from FIGS. 3 and 4, the strip-off device of the second preferred embodiment of the invention consists of a strip ring 50 which is pulled onto the expanding sleeve 3 and is adjacent to an outer shoulder 51 in the central area of the shaft cap 1. As an alternative to this, the strip ring 50 can also be axially adjacent to the groove bottom of a front groove in accordance with the foregoing embodiment.

In the second embodiment no tab or front groove is provided, however. Instead, the thread guided through the afore-described inner through bore is fastened directly at the strip ring 50 as in the latter a through bore is introduced (in longitudinal direction) through which the thread is guided and is fixed in the same. Moreover, at the outer circumference of the expanding sleeve 3 an axial bar 53 or an axial groove is formed which engages in an axial internal groove of the strip ring 50 or an axial inner bar and constitutes an axial guide for the strip ring 50. For the rest, as regards its shape the strip ring 50 is preferably adapted to the tissue clip so that the latter can be applied substantially custom-fit to the ring 50 and thus adopts a predetermined (rotary) position on the expanding sleeve 3. As a matter of course, also two threads can be provided in two function channels 42.

The functioning of the medical instrument of the second embodiment of the invention can be described as follows by way of FIG. 4.

As soon as the expanding sleeve 3 is attached to a diseased site of the organ wall (the offset tubular shaft 6 facilitates attaching the expanding sleeve 3 to a large area), the tissue clip 4 is withdrawn. To this end, the thread 11 has to be pulled along the tubular shaft 6, whereby the strip ring 50 moves forward in the direction of the distal front edge of the expanding sleeve 3. Accordingly, also the clip 4 is moved forward, until it comes off by the spring bias thereof over the distal front edge of the expanding sleeve 3 and pinches the organ tissue between its jaws.

In this context, an embodiment of a pull and/or push element alternative to the afore-described thread is referred to.

So far the releasing or withdrawing device for the tissue clip 4 has been operated by a pulling movement of the thread 11. However, it can also be the case that the operation of the operating lever 41 results in a pushing movement of the push element, whereby the releasing and withdrawing device is not pulled but pushed forward. This alternative is indicated especially in FIG. 4. In this event, for instance a wire or a flexible push rod 60 is supported in preferably two guide channels 42 disposed laterally at the tubular shaft 6 each of which is connected at its distal end to the strip ring 50. If the hinged or movably supported operating lever 41 is swiveled/shifted, this movement is transmitted to the strip ring 50 by the preferably two push rods 60 and thus the clip 4 is released.

Finally, in FIG. 5 a third preferred embodiment of the invention is shown which is based on the second embodiment. So far, hereinafter only the features that are different from the second embodiment are described.

In accordance with FIG. 5, the rigid tubular shaft 6 is not simply offset at the distal end portion, but in this area exhibits a gooseneck or S-shape, wherein the discharge direction defined by the expanding sleeve 3 is aligned at an angle (>0°) with respect to the straight tubular shaft portion in the central area and the proximal area of the tubular shaft 6.

Due to this shape, the expanding sleeve 3 can be reset with respect to an (imaginary) central line of the tubular shaft 6 in parallel hereto so that an instrument inserted into the colon of a patient does not expand or only slightly expands the organ wall.

Moreover, as indicated in FIG. 6, the holding portion 40*b* of the instrument handle 40 can be folded with respect to the tubular shaft 6. For this purpose, the holding portion 40*b* is articulated via a hinge at the mounting portion 40*a* of the handle 40 and is locked there, if necessary. By folding the handhold 40*b* a screwdriver handle position is resulting, which improves the handling of the instrument in the inserted position.

FIGS. 7 and 8 represent a tissue clip which was developed in particular for the proctological instrument according to the invention.

This clip 200 likewise consists of a mouth-type clamping means including a toothed upper jaw 210 and a toothed lower jaw 220. Concretely speaking, the clip 200 according to the invention is punched or lasered out of a sheet or steel sheet material in one piece. It comprises substantially a closed ring having the two diametrally opposed upper and lower jaw portions 210, 220 each of which is formed of a wide sheet piece and two diametrally opposed hinge portions 230, 240 arranged offset by 90° vis-à-vis the jaw portions for connecting the jaw portions 210, 220 to each other.

The jaw portions 210, 220 are shaped to have jags or teeth 250 which cross the ring and engage with each other at their longitudinal edges facing each other.

The hinge portions 230, 240 are formed of a strip-like sheet piece which is by far narrower compared to the jaw portions 210, 220 and which is arched to be substantially semi-circular to the inside along the entire circle segment circumference thereof, i.e. in the direction of the ring center. In this way two diametrally opposed semi-circular or pitch circle bulges 260, 270 are formed at the ring so as to form the hinges of the two jaw portions 210, 220.

Furthermore, the ring is bent or folded over its flat side by approx. 180° in the area of the two hinge portions. Concretely speaking, the two hinge portions 230, 240 are bent perpendicularly to the ring plane at their respective transition areas 280, 290 to the upper and lower jaws such that the semicircular or pitch circle bulge 260, 270 is aligned outwardly, viz. away from the ring center. In addition, the jaw portions 210, 220 are bent or arched equally perpendicularly to the ring plane over the entire circumferential portion thereof, but in the direction opposite to the bending direction of the hinge portions 230, 240.

This arching results in a three-dimensional ring in which the hinge portions 230, 240 are located above (at the arched outside of) the jaw portions 210, 220 and are aligned radially outwardly as well as obliquely in the direction of the jaw portions 210, 220. It is further emphasized in this context that the clip material is highly elastic at least in the area of the hinge portions 230, 240 and preferably throughout the entire clip ring.

If the clip 200 represented in FIG. 7 in the (relaxed) constructional position is elastically unfolded, i.e. the jaw portions 210, 220 are opened, an elastic deformation is imparted to the two hinge portions 230, 240 such that the semi-circular or pitch circle bulges 260, 270 are narrowed. At the same time, the hinge portions 230, 240 are twisted so that the bulges 260, 270 rotate in the direction of a 90° angle with respect to the jaw portion surfaces. By the two elastic movements spring energy is stored which biases both jaw portions 210, 220 with a predetermined closing force.

After all, the through bore 300 in either of the jaw portions 210 shown in FIG. 7 is mentioned into which a thread or a similar fastening element (not shown) can be threaded. In this case, the tissue clip 200 can be used as an anchor for a medical instrument or the like.

FIG. 8 illustrates an alternative configuration of the tissue clip 200 according to FIG. 7, wherein merely the geometrical differences from the clip 200 according to FIG. 7 shall be described hereinafter.

In the clip according to FIG. 8 the semi-circular or pitch circle bulges 260, 270 of the hinge portions 230, 240 are aligned outwardly, viz. away from the ring center, in an unbent state and thus constitute two diametrally opposed bulges at the circumference of the ring. If the hinge portions 230, 240 are bent as afore described, hereby the originally outwardly directed bulges are directed inwardly. Consequently, in the finished state of the clip 200 the bulges 260, 270 of the hinge portions 230, 240 according to FIG. 8 are aligned exactly at 180° opposite to the bulges of the hinge portions according to FIG. 7. All other geometrical features are identical and also the functioning of the tissue clip 200 according to FIG. 8 corresponds to that of FIG. 7 so that in this context the foregoing description can be referred to.

The invention claimed is:

1. A proctological instrument comprising:
an instrument handle to which at its proximal end a bending-resistant tubular shaft is mounted at the distal end of which a cap is fixed or formed to which a tissue clip adapted to be withdrawn from the cap by means of a releasing or withdrawing means is attached in a preferably spring-elastic manner, wherein the tubular shaft is offset at its distal end portion in an area directly ahead of the cap and/or the cap itself is offset at a predetermined fixed angle so that the withdrawing direction for the clip defined by the cap is aligned at the angle with respect to the tubular shaft axis, wherein the releasing or withdrawing means at least comprises a pulling/pushing element which extends along the tubular shaft within at least one function channel being fixed at the outer surface of the tubular shaft and which releasing or withdrawing means further has an operating lever which is provided at the instrument handle and which is coupled with the pulling/pushing element at the proximal end thereof, further wherein:
the bending-resistant tubular shaft is pre-bent in an S-shape at its distal end portion,
the pulling/pushing element is coupled at its distal end to a withdrawing ring which is shiftably supported on the outer surface of the cap,
two function channels are provided being arranged diametrical to each other with respect to the tubular shaft at its outside surface, and
the pulling/pushing element is formed as cables which are shiftably supported within the function channels to apply forces onto the withdrawing ring in an axially symmetrical manner.

2. The proctological instrument according to claim 1, wherein the releasing or withdrawing device includes at least one pull and/or push element extending along the tubular shaft in a respective function channel fixed at the outside of the tubular shaft and being coupled at its proximal end to an operating lever of the instrument handle and at its distal end to a slip ring which is guided so as to be axially movable on the cap.

3. The proctological instrument according to claim 1, wherein the cap at its outside includes a longitudinally extending tab forming a groove-shaped gap between itself and the outer cap wall into which gap the clip is inserted.

4. The proctological instrument according to claim 3, wherein the pull and/or push element is a thread which is guided at its distal end across the groove-shaped gap and is fixed at the tab in order to be entrained by the same when the clip is slipped on and which is mounted at its proximal end to an operating lever of the instrument handle in order to be pulled upon operation of the lever, whereby the thread portion inside the gap shrinks and thus withdraws the clip to the front.

5. The proctological instrument according to claim 1, wherein the instrument handle has a grip portion which is hinged to the instrument handle such that its angular position is adjustable with respect to the tubular shaft.

6. A tissue clip for a proctological instrument especially according to claim 1, further comprising upper and lower jaws which are elastically connected via two hinge portions while forming a closed ring, each of the hinge portions in the ring plane being in the form of a pitch circle bulge, wherein the hinge portions are bent in each transition area to the jaws by approximately 160° to 180° perpendicularly to the ring plane.

7. The tissue clip according to claim 6, wherein the bulges are aligned radially inwardly or outwardly in the bent state of the hinge portions.

8. The tissue clip according to claim 6, wherein the jaws are bent perpendicularly to the ring plane in a direction opposed to the bending direction of the hinge portions so as to obtain a bulge.

9. The tissue clip according to claim 7, wherein the jaws are bent perpendicularly to the ring plane in a direction opposed to the bending direction of the hinge portions so as to obtain a bulge.

* * * * *